United States Patent [19]

Himmelmann

[11] 4,116,700
[45] Sep. 26, 1978

[54] PROCESS FOR HARDENING PHOTOGRAPHIC LAYERS

[75] Inventor: Wolfgang Himmelmann, Leverkusen, Germany

[73] Assignee: AGFA-Gevaert, A.G., Leverkusen-Bayerwerk, Germany

[21] Appl. No.: 786,470

[22] Filed: Apr. 11, 1977

[30] Foreign Application Priority Data

Apr. 14, 1976 [DE] Fed. Rep. of Germany ....... 2616376

[51] Int. Cl.$^2$ ................................................ G03C 1/30
[52] U.S. Cl. .................................. 96/111; 96/50 PT; 96/77; 106/125; 260/117
[58] Field of Search ...................... 96/111, 77, 50 PT; 260/117; 106/125

[56] References Cited

U.S. PATENT DOCUMENTS

| | | | |
|---|---|---|---|
| 3,325,287 | 6/1967 | Yamamoto et al. | 96/111 |
| 3,549,377 | 12/1970 | Meckl et al. | 96/111 |

FOREIGN PATENT DOCUMENTS 2,500,427  7/1975  Fed. Rep. of Germany ............. 96/111

OTHER PUBLICATIONS

Nohara et al.: Derivatives of Ditraizinylamine and Tri-triazinylamine, J. Heterocycl. Chem., vol. 7 (1970), pp. 519–525.

Primary Examiner—Won H. Louie, Jr.
Attorney, Agent, or Firm—Connolly and Hutz

[57] ABSTRACT

In a process for hardening photographic layers which contain protein and in particular gelatine partially hydrolyzed bis-(dichlorotriazin-2-yl)-alkylamines or -arylamines are used as hardeners.

10 Claims, No Drawings

PROCESS FOR HARDENING PHOTOGRAPHIC LAYERS

This invention relates to a process for hardening photographic layers which contain protein, preferably gelatine.

Several substances have already been described as hardeners for proteins and in particular for gelatine, for example metal salts such as chromium, aluminium or zirconium salts, aldehydes and halogenated aldehyde compounds, in particular formaldehyde, dialdehydes and mucochloric acid, 1,2- and 1,4-diketones such as cyclohexane dione-(1,2) and quinones, chlorides of dibasic organic acids, anhydrides of tetracarboxylic acids, compounds having several reactive vinyl groups such as vinyl sulphones, acrylamides, compounds having at least two heterocyclic three-membered rings which are easily split off such as ethylene oxide and ethyleneimine, polyfunctional methane sulphonic acid esters and bis-α-chloroacylamido compounds.

High molecular weight hardeners such as polyacrolein and its derivatives or copolymers and alginic acid derivatives have recently become known. These are used more particularly as hardeners which are restricted to their layer.

The use of the above mentioned compounds for photographic purposes, however, entails numerous serious disadvantages. Some of these compounds are unsuitable for hardening photographic materials because they are photographically active while others cannot be used because they have a harmful effect on the physical properties of the gelatine layers, for example on their fragility. Others again cause discolorations or a change in pH during the hardening reactions. Furthermore, for hardening photographic layers it is particularly important that the hardening effect should reach its maximum as soon as possible after drying so that the photographic material will not continuously change its permeability to the developer solution as in the case, for example, of mucochloric acid or of formaldehyde.

Some cross-linking agents for gelatine also have a damaging effect on the skin, for example ethylene imine compounds, and their use is therefore contraindicated on physiological grounds.

Finally, when choosing a hardener for photographic layers containing gelatine, it is most important both for manufacturing reasons and for reasons of processing, that the onset of the cross-linking reaction should be predeterminable within certain limits, for example by choice of the drying temperature or of the pH.

Compounds having two or more acrylic acid amido or vinyl sulphone groups in the molecule are also known as hardeners for photographic gelatine layers, for example divinylsulphone, arylene-bis-vinylsulphones, N,N',N''-trisacryloyl-hydrotriazine and methylene-bis-vinyl sulphonamide.

Although these compounds effect sufficient hardening in the course of time, they are difficult to dissolve in water, with the result that the layers are likely to be unevenly hardened.

The consequences of the above mentioned undesirable properties of known hardeners are extremely important from the photographic point of view because important photographic properties such as gradation and sensitivity and in many cases also the silver covering power depend on the degree of cross-linkage of the layer forming colloid and undergo change during storage. Although this disadvantage can be attenuated by a brief after-treatment of the solidified layer with ammonia or an amine, it cannot be completely eliminated. To this is added the fact that aliphatic divinyl sulphones have properties which are damaging to the skin.

Carbodiimides have also long been known as hardeners for photographic materials. Non-ionic carbodiimides have been described in DDR Patent Specification No. 7218 as hardeners for photographic proteins. The iodides of carbodiimides which have amino groups have been disclosed in German Patent Specification No. 1,148,446 and toluene and methylsulphonates in U.S. Pat. No. 3,100,704. Combinations of gelatine and carbodiimides with polymers which contain carboxylic acid have been mentioned in British Patent No. 1,272,587.

Hardening of gelatine using 1-ethyl-3-dimethylaminopropyl-carbodiimide hydrochloride has been described in the publication by Robinson in Journal of Photographic Science Vol. 16 (1968), page 41.

All carbodiimide compounds are to some extent suitable as rapid hardeners but they have photographic and toxicological disadvantages. The non-ionic carbodiimides such as dicyclohexyl carbodiimide or diisopropyl carbodiimide are difficultly soluble and are irritants to the skin. The urea compounds formed in the reaction separate from the layer and cause cloudiness. Moreover, the simpler carbodiimides are known to be allergens. Carbodiimides must be made water-soluble before use by the introduction of amino groups. The compounds which contain amino groups are photographically active and still have a physiological activity. They lower the sensitivity after storage and increase the photographic fog in colour emulsions which contain emulsified colour couplers. Finally, the water-soluble carbodiimides which contain amino groups react with phenolic cyan colour components, thereby reducing the final densities.

Lastly, cyanuric chloride and aminodichlorotriazine are known as hardeners for photographic layers containing gelatine. Their active principle may be represented by the following formula (Photographic Abstracts, Volume 28 (1948), page 63):

Water-soluble anionic groups were introduced to improve the solubility and reduce the vapour pressure of the physiologically active compounds, e.g. as follows:

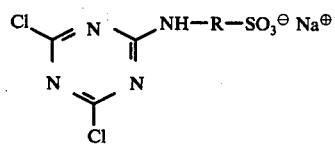

These compounds, however, were found to be less reactive because the introduction of an amino group into the triazine group reduces the activity of the halogen. Alkali metal and alkaline earth metal salts of hydroxy dichlorotriazine

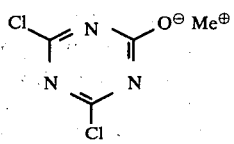

have also been proposed as hardeners, in German Auslegeschrift No. 1,284,290. However, these compounds are not stable in the solid form and have to be stocked as aqueous solutions. The reactivity of the halogen atom is higher in these compounds than in the compounds mentioned above and the compounds therefore cannot be digested in concentrated gelatine solutions for any length of time without increasing the viscosity of the solution. This leads to serious disadvantages when casting the photographic materials because the thickness of the layer increases with the viscosity so that a continuous casting process cannot be maintained over a long period.

Substituted urea derivatives typically exemplified by compounds of the following formulae:

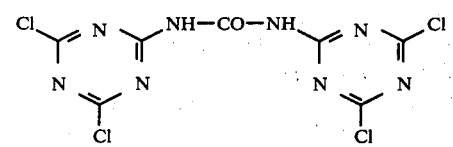

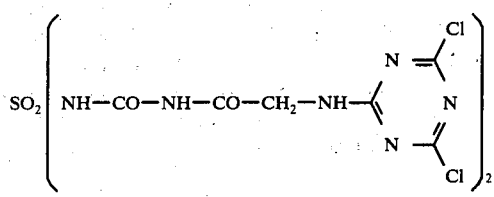

have recently been suggested as cross-linking agents for synthetic resins and gelatine as described in German Offenlegungsschrift No. 2,500,427. Representatives of both these classes of compounds are insoluble in water and do not produce stable cross-linkages when photographic materials are processed at 38° C. The bonds dissolve and hardening regresses.

It is an object of the present invention to develop a process for hardening photographic layers which on the one hand reduces or substantially obviates the difficulties arising from viscosity changes occurring when the hardener is used in the casting composition and, on the other hand, gives rise to layers which reach their final degree of hardening within a relatively short time after drying.

The invention relates to a process for hardening photographic layers which contain protein and in particular gelatine, characterised in that the hardeners used are partially hydrolysed bis-(dichlorotriazin-2yl)-alkylamines or -arylamines.

The hardeners used according to the invention are represented by the following general formula

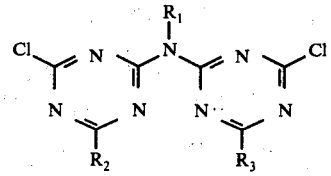

in which
$R_1$ represents hydrogen, alkyl with 1 to 3 carbon atoms which may be substituted with hydroxyl or halogen, alkoxyalkyl with 2 to 5 carbon atoms such as methoxyalkyl or ethoxyalkyl, cycloalkyl such as cyclopentyl or cyclohexyl, aryl such as phenyl or naphthyl which may be substituted with methyl, oxymethyl, halogen, methoxycarbonyl or ethoxycarbonyl, nitro, aralkyl such as phenylmethyl or a group of the formula

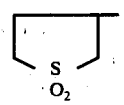

$R_2$ represents Cl or $R_3$
$R_3$ represents hydroxyl or $-O^- Me^+$ in which $Me^+$ represents an alkali metal or ammonium ion. The following compounds are examples of hardeners which are suitable for the process according to the invention:

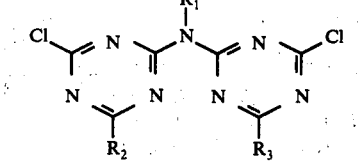

| Compound | $R_1$ | $R_2$ | $R_3$ |
|---|---|---|---|
| 1. | $-C_2H_5$ | Cl | $-ONa$ |
| 2. | $-C_2H_5$ | $-ONa$ | $-ONa$ |
| 3. | H | Cl | $-ONa$ |
| 4. | H | $-ONa$ | $-ONa$ |
| 5. | $-CH_3$ | Cl | $-ONa$ |
| 6. | $-CH_3$ | $-ONa$ | $-ONa$ |
| 7. | $-CH_2-CH_2-OCH_3$ | $-ONa$ | $-ONa$ |
| 8. | 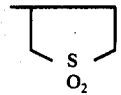 | Cl | $-ONa$ |
| 9. | 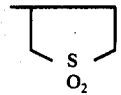 | $-ONa$ | $-ONa$ |
| 10. | $-(CH_2)_3-OC_2H_5$ | $-ONa$ | $-ONa$ |
| 11. | $-CH_3$ | $-OLi$ | $-OLi$ |
| 12. | $-CH_2-CH_2-OH$ | $-ONa$ | $-ONa$ |
| 13. | $C_6H_5-$ | $-ONa$ | $-ONa$ |
| 14. | $o-CH_3C_6H_4-$ | $-ONa$ | $-ONa$ |
| 15. | $p-CH_3C_6H_4-$ | $-ONa$ | $-ONa$ |
| 16. | $2,6(CH_3)_2C_6H_3-$ | $-ONa$ | $-ONa$ |
| 17. | 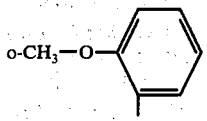 | $-ONa$ | $-ONa$ |
| 18. | $p-CH_3OC_6H_4-$ | $-ONa$ | $-ONa$ |
| 19. | $o-ClC_6H_4-$ | $-ONa$ | $-ONa$ |
| 20. | $p-ClC_6H_4-$ | $-Ona$ | $-ONa$ |

-continued

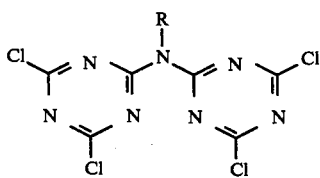

| Compound | R₁ | R₂ | R₃ |
|---|---|---|---|
| 21. | CH₃O—CO—⟨phenyl⟩— | —ONa | —ONa |
| 22. | CH₃—O—CO—⟨phenyl⟩— | —ONa | —ONa |
| 23. | O—NO₂C₆H₄— | —ONa | —ONa |
| 24. | I—C₁₀H₇— | —ONa | —ONa |
| 25. | ⟨cyclopentyl⟩ | —ONa | —ONa |
| 26. | Cl—(CH)₃— | —ONa | —ONa |
| 27. | o-CH₃—C₆H₄— | —Cl | —ONa |
| 28. | CH₃—O—⟨phenyl⟩— | —Cl | —ONa |
| 29. | ⟨o-Cl-phenyl⟩ | —Cl | —ONa |
| 30. | CH₃O—CO—⟨phenyl⟩— | —Cl | —ONa |

The compounds are new and are prepared by partial hydrolysis of tetrahalgen compounds of the following formula which have been described in J. Heterocycl. Chem. Vol. 7 (1970), page 519:

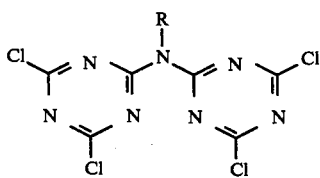

Partial hydrolysis is carried out in aqueous solution with the addition of bicarbonate. The hardening compounds are obtained directly so that the bis-triazine salt need not be separated, purified or redissolved.

The surprising advantage of these compounds is that the reactivity of the halogen atoms is not so greatly reduced by introduction of the triazinylamino group as by introduction of an alkylamino group, nor is it so high as in the presence of cyanuric chloride, that the casting solution undergoes an increase in viscosity and irreversible coagulation. The compounds according to the invention do not affect the photographic properties and their hardening action is not reduced by the presence of other additives. The compounds are therefore particularly suitable for use as hardeners for layers which contain colour couplers. The compounds according to the invention have the advantage, compared with hydrox-ydichlorotriazine, that they are also stable in the solid form and can be stored in this form.

The preparation of amino, alkylamino and arylamino dichlorotriazines has been disclosed in
Ber. 32 [1899] 695,
Am.Soc. 67 [1945] 663,
B. 19 243.

Reaction of aminodihalogentriazines with cyanuric chloride gives rise to bistriazinylimines:

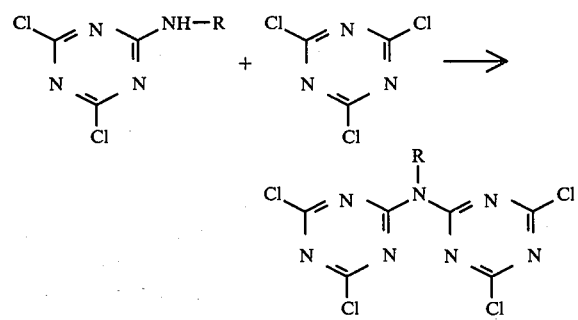

Hydrolysis of these compounds can be carried out, for example, with sodium bicarbonate:

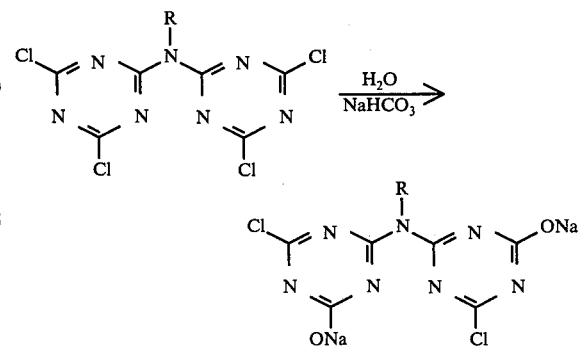

Bis(tetrahalogentriazinyl)-amines are hydrolysed to trihalogenhydroxy and dihalogendihydroxy compounds under comparatively mild conditions. Hydrolysis comes to a standstill at this stage and there is practically no formation of tetra or trihydroxy compounds, which no longer act as hardeners. The salts need not be isolated since they are stable for several months in aqueous solution in the presence of bicarbonate solution without losing their hardening activity. The need for separation and purification of the bis-triazinylamines is therefore obviated. The compounds can also be isolated in their pure form or in the solid form, as will be described hereinafter.

The process for preparing the compounds according to the invention will be explained in detail in the examples which follow.

Preparation of
ethyl-bis-(4,6-dichloro-s-triazin-2-yl)-amine Starting compound A 3

A solution of 0.4 g of sodium hydroxide in 4 ml of water was added dropwise with stirring over a period of 20 minutes to a solution of 1.93 g of 2-ethylamino-4,6-dichlorotriazine and 1.85 g of cyanuric chloride in 50 cc of acetone which had been cooled to 0°–5° C. Stirring was continued for 6 hours after all the sodium hydroxide solution had been added. The resulting solution was then neutralised with sodium carbonate and stirred into ice water. The precipitate was collected, dried and recrystallised from ligroin.

Yield: 2.2 g, m.p. 143° C.

Preparation of Compound 1

10.2 g of the above compound A 3 were dissolved in 70 ml of acetone. The solution was introduced dropwise into a solution of 7.5 g of sodium bicarbonate in 200 ml of water at 35° C. with vigorous stirring. Stirring of the mixture at 35° C. was continued. After 6 hours, a small quantity of insoluble residue was filtered off. The acetone was then evaporated off in a rotary evaporator and water was added. The contents of the solution depend on the quantity put into the process. 2% solutions can be prepared in this way.

Preparation of Compound 2

10.2 g of the starting compound A 3 were dissolved in 70 ml of acetone and introduced dropwise into a solution of 15 g of sodium bicarbonate and 200 ml of water at room temperature with stirring. The mixture was then heated to 60° C. for 6 hours, during which time all of the substance went into solution. The acetone was evaporated off and water was added if necessary. The solution has a concentration of 3%.

Preparation of starting compound A 12

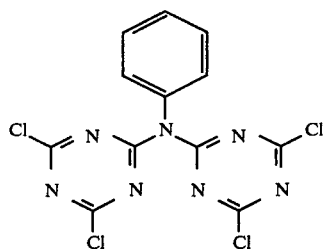

A solution of
4.8 g of sodium hydroxide in
48 cc of water was introduced dropwise at 0° to 5° C. with stirring into a solution of
32.2g of dichlorotriazinylanilide and
22.2g of cyanuric chloride in
400cc of acetone.

The mixture was then stirred at 0° to 5° C. for 5 hours and precipitated in a solution of
12 g of sodium bicarbonate in
2 l of ice water. The precipitated product was washed, dried and recrystallised from a mixture of water and acetone.

Melting point: 178° to 180° C.

Preparation of Compound 13

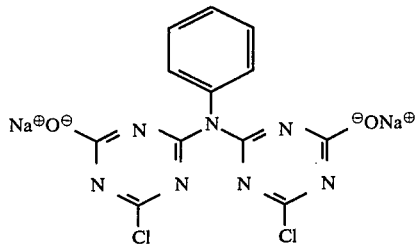

11.7g of Compound A 12 were dissolved in
70 cc of acetone, filtered and introduced dropwise into a solution of
15 g of sodium bicarbonate in
400cc of water.

The mixture was stirred at 60° C. for 24 hours. The resulting solution was filtered with microfil, the acetone present was evaporated off under vacuum and the remaining solution was adjusted to a concentration of 3.5%.

Preparation of starting compound A 8

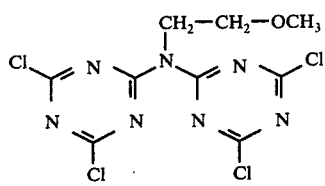

A solution of
4.8 of sodium hydroxide in
48 ml of water was added dropwise at 0° to 5° C. over a period of 30 minutes with vigorous stirring to a solution of
27.1 g of dichloromethoxyethylaminotriazine and
22.2 g of cyanuric chloride in
400 ml of acetone, The mixture was then stirred for 5 hours in an ice bath and precipitated in a solution of
12 g of sodium bicarbonate in
2 l of ice water.

The precipitated product was suction filtered, thoroughly washed with water and dried in air.

Yield: 32 g; melting point: 85° to 95° C.

Preparation of Compound 7

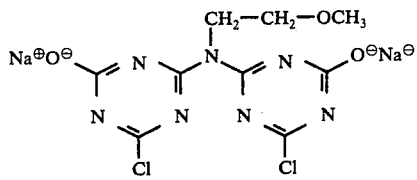

11.1 g of compound A 8 were dissolved in
70 ml of acetone and introduced dropwise into a mixture of
15 g of sodium bicarbonate in
400 ml of water. The mixture was stirred for about 7 hours at 60° C. A clear solution was obtained.

The acetone was evaporated off under vacuum.
The solution was adjusted to a concentration of 3.3%.

Isolation of compound 7 in solid form 300 ml of a 7.5% solution of compound 7 were concentrated to about half its volume by evaporation under vacuum at a temperature of not more than 50° to 60° C. The mixture was cooled and the crystalline product which precipitated was suction filtered. It was then recrystallised from a small quantity of water and dried in air.

Yield: 12 g, m.p.: above 220° C.

When dry the product can be stored in a glass bottle without evolution of hydrogen chloride.

The following starting compounds for the compounds of the invention mentioned previously as examples can easily be prepared by this method.

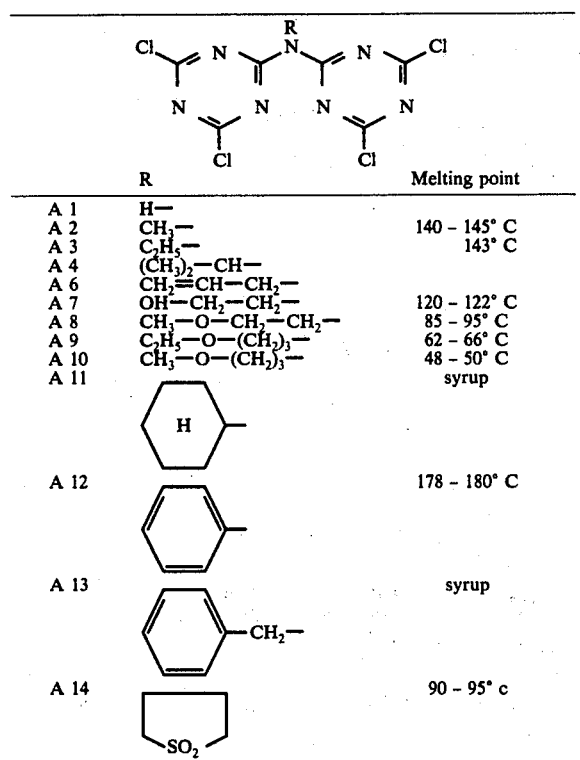

| | R | Melting point |
|---|---|---|
| A 1 | H— | |
| A 2 | CH₃— | 140 – 145° C |
| A 3 | C₂H₅— | 143° C |
| A 4 | (CH₃)₂—CH— | |
| A 6 | CH₂=CH—CH₂— | |
| A 7 | OH—CH₂—CH₂— | 120 – 122° C |
| A 8 | CH₃—O—CH₂—CH₂— | 85 – 95° C |
| A 9 | C₂H₅—O—(CH₂)₃— | 62 – 66° C |
| A 10 | CH₃—O—(CH₂)₃— | 48 – 50° C |
| A 11 | | syrup |
| A 12 | | 178 – 180° C |
| A 13 | | syrup |
| A 14 | | 90 – 95° c |

The preparation of other aryl compounds including those indicated in the following table has been described in J. Heterocycl. Chem. Vol. 7 (1970):

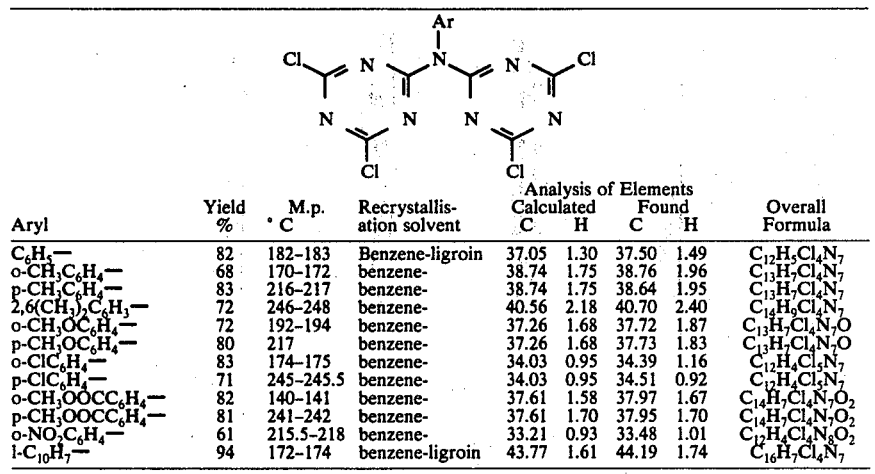

| Aryl | Yield % | M.p. °C | Recrystallisation solvent | Analysis of Elements Calculated C | H | Found C | H | Overall Formula |
|---|---|---|---|---|---|---|---|---|
| C₆H₅— | 82 | 182–183 | Benzene-ligroin | 37.05 | 1.30 | 37.50 | 1.49 | C₁₂H₅Cl₄N₇ |
| o-CH₃C₆H₄— | 68 | 170–172 | benzene- | 38.74 | 1.75 | 38.76 | 1.96 | C₁₃H₇Cl₄N₇ |
| p-CH₃C₆H₄— | 83 | 216–217 | benzene- | 38.74 | 1.75 | 38.64 | 1.95 | C₁₃H₇Cl₄N₇ |
| 2,6(CH₃)₂C₆H₃— | 72 | 246–248 | benzene- | 40.56 | 2.18 | 40.70 | 2.40 | C₁₄H₉Cl₄N₇ |
| o-CH₃OC₆H₄— | 72 | 192–194 | benzene- | 37.26 | 1.68 | 37.72 | 1.87 | C₁₃H₇Cl₄N₇O |
| p-CH₃OC₆H₄— | 80 | 217 | benzene- | 37.26 | 1.68 | 37.73 | 1.83 | C₁₃H₇Cl₄N₇O |
| o-ClC₆H₄— | 83 | 174–175 | benzene- | 34.03 | 0.95 | 34.39 | 1.16 | C₁₂H₄Cl₅N₇ |
| p-ClC₆H₄— | 71 | 245–245.5 | benzene- | 34.03 | 0.95 | 34.51 | 0.92 | C₁₂H₄Cl₅N₇ |
| o-CH₃OOCC₆H₄— | 82 | 140–141 | benzene- | 37.61 | 1.58 | 37.97 | 1.67 | C₁₄H₇Cl₄N₇O₂ |
| p-CH₃OOCC₆H₄— | 81 | 241–242 | benzene- | 37.61 | 1.70 | 37.95 | 1.70 | C₁₄H₇Cl₄N₇O₂ |
| o-NO₂C₆H₄— | 61 | 215.5–218 | benzene- | 33.21 | 0.93 | 33.48 | 1.01 | C₁₂H₄Cl₄N₈O₂ |
| 1-C₁₀H₇— | 94 | 172–174 | benzene-ligroin | 43.77 | 1.61 | 44.19 | 1.74 | C₁₆H₇Cl₄N₇ |

The compounds used according to the invention may be added to the protein layers which they are required to harden before the layers are cast and preferably in the form of aqueous solutions. The viscosity of the gelatine-containing solutions undergoes practically no change within the first few hours after addition of the compounds. It is only when the layers are dry that the cross-linking reaction suddenly accelerates and reaches its maximum after a few days. Another possible method of applying the compounds according to the invention consists in casting the solutions before they have been hardened and then covering the resulting layers with a solution of the hardening compound. Alternatively, photographic layers which have not yet been hardened or only slightly hardened may be bathed in an aqueous solution containing the compounds and sodium sulphate during photographic processing, for example, before development.

The hardeners according to the invention can be used in combination with high boiling, water-soluble organic solvents used as plasticizers for gelatine.

These solvents are used either separately or together with the hardeners. Suitable solvents for this purpose include e.g. glycerol, trimethylolpropane, pyrrolidone and dimethylformamide. Since the layers in this case retain water for a longer time during the drying process, cross-linking proceeds at a higher velocity.

By photographic layers are meant in this context any layers in general which are used in photographic materials, for example light-sensitive silver halide emulsion layers, protective layers, filter layers, antihalation layers, back coating layers or any photographic auxiliary layers.

Light-sensitive emulsion layers which are particularly suitable for the hardening process according to the invention include, for example, layers based on unsensitized emulsions, orthochromatic, panchromatic or infra-red emulsions, X-ray emulsions and other spectrally sensitized emulsions. The hardening process according to the invention has also been found suitable for hardening the gelatine layers used for various black-and-white and colour photographic processes. The process according to the invention has proved to be particularly advantageous for hardening photographic layer combinations used for carrying out colour photographic processes, for example, combinations having emulsion layers which contain colour couplers or combinations having emulsion layers which are intended to be treated with solutions which contain colour couplers.

The action of the compounds used according to the invention is not impaired by the usual photographic additives. The hardeners are inert towards photographically active substances such as water-soluble and emulsified colour components, stabilizers and sensitizers. The compounds have no influence on the light-sensitive silver halide emulsions and they can be combined with any of the compounds belonging to the various known series of hardeners, for example formalin, mucochloric acid, triacryloformal, bis-vinyl sulphones, bis-vinyl sulphonamides, dialdehydes, bis-chloroacetamides and hardeners which act by alkylation of carboxyl groups, e.g. carbamoyl pyridinium salts, carbamoyloxypyridinium salts or isoxazolium compounds.

Apart from gelatine, the layers may contain water-soluble high polymer compounds, in particular polyvinyl alcohol, polyacrylic acid sodium and other copolymers containing carboxyl groups, also polyvinyl pyrrolidone, polyacrylamide or high molecular weight naturally occurring substances such as dextrans, dextrins, starch ethers, alginic acid and alginic acid derivatives.

The compounds according to the invention are applied as aqueous coatings or introduced by addition into the casting solutions.

The concentrations at which the hardeners according to the invention are used may vary within wide limits and depend mainly on the individual hardening compound used.

Satisfactory results are generally obtained with quantities of from 0.1 to 10% by weight and particularly 0.1 to 8% by weight, based on the dry weight of binder, particularly if the hardener is incorporated in the casting composition of the layer which is required to be hardened. As already mentioned above, the hardening reaction between the compounds of the invention and gelatine or proteins sets in immediately after drying.

The effect of the hardening compounds is assessed from the melting point of the layers, which is determined as follows:

A layer which has been cast on a support is half dipped in water which is continuously heated to 100° C. The temperature at which the layer runs off the substrate (formation of streaks) is taken as the melting point or melting off point. When measured by this method, pure protein or gelatine layers containing no hardener in no case show an increase in melting point. The melting off point obtained under these conditions lies in the range of 30° to 35° C.

Compared with cyanuric chloride, the compounds according to the invention harden gelatine in aqueous solution more slowly, with the result that the viscosity of the solutions does not increase unduly and irreversible solidification of gelatine does not take place. It was not expected that the compounds according to the invention would be extremely well cross-linked in the dry gelatine layer in spite of the slower reaction in aqueous gelatine solution. This has the following interesting advantages for practical purposes.

Compared with cyanuric chloride, the compounds have the advantage of being water-soluble. They do not require to be applied as covering layers of solvent-containing solutions. Compared with hydroxy dichlorotriazine, they have the advantage of being stable in the solid form. Moreover, the compounds can be produced in large quantities and stored solvent-free.

In their velocity of hardening, the compounds according to the invention are intermediate between cyanuric chloride and hydroxydichlorotriazine. This difference between the compounds according to the invention and hydroxydichlorotriazine is due to the fact that, in the compounds according to the invention, the reaction with the amino groups of gelatine takes place on different triazine groups. The difference in the cross-linking velocity of aqueous gelatine solutions can be demonstrated by the following comparison experiments.

Equimolar quantities of cyanuric chloride, hydroxydichlorotriazine and compound 7 according to the invention which is represented by the following formula

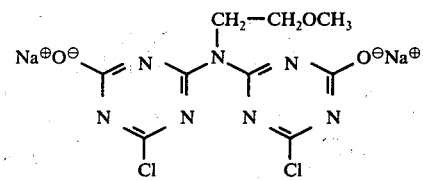

are added to separate portions of a 10% gelatine solution at pH 9 and 40° C.

The compound according to the invention is added in a quantity of 30%, based on the quantity of gelatine, while cyanuric chloride and hydroxydichlorotriazine are added in the corresponding molar quantities. The time taken for solidification of the gelatine solution at 40° C. and pH 9 is determined. The following results are obtained:

1. Compound 7 according to the invention: 150 minutes
2. Cyanuric chloride: 0 to 1 minute.
3. Hydroxydichlorotriazine (as sodium salt): 300 minutes.

The following Examples serve to explain the hardening process according to the invention.

EXAMPLE 1

A 20% by weight zein solution was prepared in a mixture of ethanol and water (8:2) and cast on the back of a cellulose acetate film. The layer obtained after drying was readily soluble in a mixture of ethanol and water. When 3% by weight of compound 4 were added to the zein solution before the mixture was cast, and the cast layer was dried and stored for one day at 35° C. and 96% relative humidity, the layer obtained was insoluble in all solvents and effectively cross-linked.

EXAMPLE 2

The hardener specified in the following Table was added in quantities of 1/200 mol, 1/100 mol and 1/50 mol per 100 g of gelatine to an unhardened silver halide emulsion containing 10% by weight of gelatine as binder. The mixture was cast on a triacetyl cellulose substrate in the usual manner and dried. The emulsion also contained the usual additives.

The layers were then tested to determine the melting points, swelling values and wet scratch resistances. The results are summarized in the following Table.

The swelling values were determined gravimetrically after 10 minutes treatment of the layers in distilled water at 22° C. and the results given as percentages.

To determine the wet scratch resistance, a metal tip of specified size was moved over the wet layer and loaded with masses of increasing weight. The wet scratch resistance was expressed in terms of the weight at which the tip left a visible scratch mark on the layer. A large weight corresponds to high wet scratch resistance and hence a high degree of hardening.

| Figures refer to 100 g of gelatine | After storage of the layer | | | | | |
|---|---|---|---|---|---|---|
| | 3 days at 22° C and 34% r.h. | | | 1½ days at 57° C and 34% r.h. | | |
| | Melting point | Swelling in % | Wet scratch resistance (p) | Melting point | Swelling in % | Wet scratch resistance (p) |
| Compound 6 | | | | | | |
| 1/200 Mol | 40° | — | — | | 430 | 750 (300) |
| 1/100 Mol | 10'100° | 590 | 400 (100) | 10'100° | 350 | 950 (850) |
| 1/50 Mol | 10'100° | 580 | 600 (300) | | 330 | 1200(1000) |
| Compound 7 | | | | | | |
| 1/200 Mol | 40° | — | — | | 475 | 650 (100) |
| 1/100 Mol | 7'100° | 690 | 700 (50) | 10'100° | 380 | 1050 (500) |
| 1/50 Mol | 10'100° | 520 | 600 (300) | | 300 | 1200(1050) |
| Compound 5 | | | | | | |
| 1/200 Mol | 38°— | — | — | 520 | 450 (50) | |
| 1/100 Mol | 83° | — | — | 10'100° | 410 | 650 (250) |
| 1/50 Mol | 10'100° | 540 | 350 (125) | | 370 | 950 (550) |
| Compound 8 | | | | | | |
| 1/200 Mol | 40° | — | — | | 530 | 450 (50) |
| 1/100 Mol | 50° | — | — | 10'100° | 530 | 500 (150) |
| 1/50 Mol | 6'100° | 520 | 300 (125) | | 350 | 850 (450) |

| | After 3 days storage at 22° C and 34% r.h. | | |
|---|---|---|---|
| | Melting point | Swelling in % | Wet scratch resistance (p) |
| Comparison without addition of hardener: | 36° | 600–800 | 100 |

The wet scratch resistance was determined in water at 22° C and in a developer of the composition given below at 38° C (values in round brackets).
10'100° means: The layers have not dissolved after 10 minutes in boiling water.

Composition of developer:
| | |
|---|---|
| Water | 950 ml |
| Sodium hexametaphosphate | 2 g |
| Sodium sulphite sicc. | 2 g |
| 10% sodium hydroxide | 5.5 ml |
| 4-amino-(N-ethyl-N-β-methane sulphonamido-ethyl)-m-toluidine sesquisulphate monohydrate | 5 g |
| Potassium bromide | 1 g |
| Sodium hydrate monohydrate | 50 g |
| Water up to | 1000 ml |

It can be seen from the table that the compounds according to the invention are highly active hardeners, particularly after brief storage at 57° C. The wet strength of layers hardened by the process according to the invention is surprisingly high. The photographic properties are comparable to those of the comparison samples. The sensitivity decreases not at all or only insignificantly after hardening. Photographic fogging was not observed.

EXAMPLE 3

20% by weight, based on the quantity of gelatine, of a magenta coupler of the following formula:

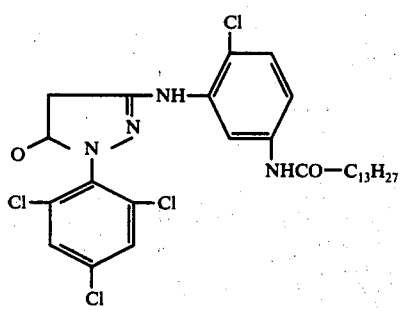

were added in emulsified form with crystalloid dibutyl phthalate (1:1) to an unhardened silver halide emulsion which contained 10% by weight of gelatine.

The usual casting additives with the exception of hardener were then added to the emulsion. The mixture was cast on a previously prepared polyethylene terephthalate substrate and dried.

Samples of this layer were then covered with aqueous solutions of compounds according to the invention. Layers which were exceptionally highly cross-linked were obtained after drying and 36 hours' storage at 57° C. and 34% relative humidity. The results are given in the following tables.

| Covering Solutions | Melting point | Swelling in % | Wet scratch resistance in p at 22° C H₂O |
|---|---|---|---|
| Compound 6 1/100 mol/100cc | 10'100° C | 330 | 450 |
| Compound 2 | 10'100° C | 310 | 400 |
| Compound 5 | 10'100° C | 340 | 450 |
| Compound 11 | 10'100° C | 320 | 400 |
| Compound 13 | 10'100° C | 380 | 350 |
| Compound 9 | 10'100° C | 390 | 350 |
| treated only with water | 42° C | 800 | — |

After storage in a tropical cupboard, swelling was reduced to 2.60–2.70. The photographic properties were not affected.

EXAMPLE 4

The usual additives except hardener were added to 100 ml of a photographic silver bromide gelatine emulsion containing 10% by weight of gelatine. The mixture was cast
(a) on baryta paper and
(b) on paper backed on both sides with polyethylene.

After drying, samples of the two materials were bathed for 2 minutes in aqueous sodium bicarbonate solutions (3% by weight) each containing 3 g of one of the compounds 1, 2, 5, 13, 10 or 11 in 100 ml of water at 20° C. The layers obtained after drying and 36 hours' storage at 57° C./34% relative humidity were in all cases fast to boiling (layer melting points 100° C.). The hardening effect obtained is independent of the substrate used. Untreated layers melt at 37° C.

EXAMPLE 5

An unhardened multilayered colour film consisting
1. a red sensitive first layer 4μ in thickness containing per kg of emulsion 35 g of silver bromide, 80 g of gelatine and 24 g of compound $K_1$ mentioned below,
2. an intermediate layer of gelatine 2μ in thickness,
3. a 4μ thick green sensitive middle layer containing per kg of emulsion 35 g of silver bromide, 80 g of gelatine and 16 g of compound $K_2$ mentioned below,
4. a 2μ filter yellow layer of colloidal silver in gelatine,
5. a 4μ blue-sensitive top layer containing per kg of emulsion 35 g of silver bromide, 80 g of gelatine and 20 g of compound $K_3$ mentioned below, and
6. a 2μ thick protective layer of gelatine was cast in the usual manner on a support layer of cellulose triacetate 120μ in thickness and dried.

The film was covered with a sodium bicarbonate solution (2.5% by weight) containing 1/100 mol of one of the compounds 1, 2 or 5, per 100 cc. The layer melting points at temperatures at which the layer becomes detached were determined after drying and after storage for 36 hours at 57° C./34% relative humidity.

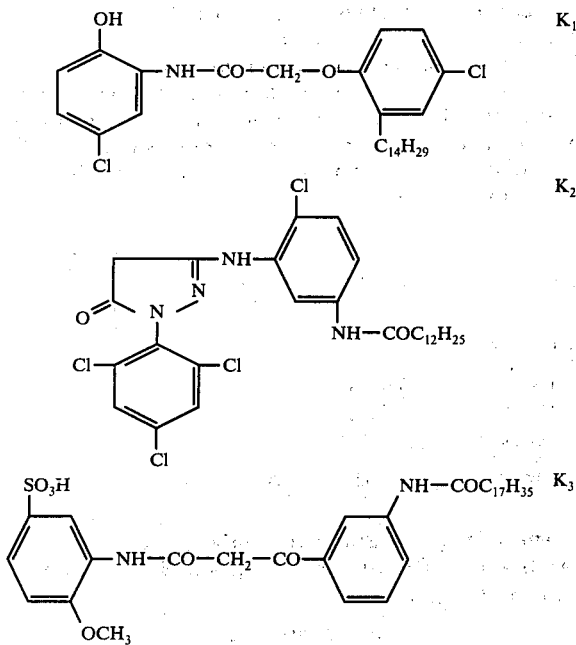

| Covering solution | Temperature at which layer becomes detached | Layer melting point |
|---|---|---|
| Compound 2 | >100° C | 10'100° C |
| Compound 5 | >100° C | 10'100° C |
| Compound 1 | >100° C | 10'100° C |
| Comparison material | not covered | 40° C | 40° C |

The results show that the cast multilayered photographic material is effectively cross-linked by the covering solution down to the lowermost layers.

EXAMPLE 6

40 ml of a 5% aqueous solution of polyacrylic acid sodium and 10 ml of a 40% silica suspension were added to 100 ml of a 10% gelatine solution. The solution was thoroughly mixed. To separate 100 ml portions of the solution were then added 0.2 g of compounds 2 and 6, respectively, the pH was adjusted to 6.2 and the mixtures were cast on a cellulose triacetate substrate. A layer having a melting point above 100° C. and excellent wet strength was obtained after drying and 12 hours' storage. A layer without the addition of compounds according to the invention was found to have a melting point of 40° C. in water.

EXAMPLE 7

To 100 ml of a 10% aqueous solution of acetyl gelatine prepared by reacting gelatine with 20% acetic anhydride were added in each case 0.2 g of compound 1 and 0.2 g of compound 10, respectively, and the mixture was cast on a cellulose acetate film. A layer containing 0.2 g of formalin instead of compound 1 or 10 was used for comparison. The layers containing compounds 1 and 10 were fast to boiling after drying. Layers hardened with formalin had a melting point below 100° C.

EXAMPLE 8

50 g of compound 7 and 50 g of the comparison compound

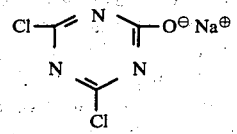

which is not in accordance with the invention were dried in air and then stored in a sealed glass bottle for 3 days at room temperature. The comparison compound decomposed with evolution of hydrogen chloride and could not be stored under these conditions. The compound according to the invention did not release hydrogen chloride and was stable under the given conditions. The comparison compound can therefore only be prepared in the form of aqueous solutions if required in large quantities. This is a serious commercial disadvantage of the compound compared with the compounds according to the invention.

EXAMPLE 9

An unhardened multilayered colour film of the kind described in Example 5 was covered with the following solutions of hardeners:
1. 1/100 mol of Compound 6
   0.2 g of saponin and 1 g of sodium bicarbonate
   100 cc of water
2. 1/100 mol of Compound 6
   0.2 g of saponin and 1 g of sodium bicarbonate
   100 cc of water
   3 g of pyrrolidone-2

3. 1/100 mol of Compound 6
0.2 g of saponin and 1 g of sodium bicarbonate
100 cc of water
3 g of glycerol
4. 1/100 mol of Compound 7
0.2 g of saponin and 1 g of sodium bicarbonate
100 cc of water
3 g of trimethylolpropane.

The film was covered with the solutions and then dried. The thickness of the wet layer was the same in all cases. The layer melting point, swelling factor and wet scratch resistance at 20° C. in water and at 38° C. in the colour developer were determined after drying and storage of the samples at 57° C. and 34% relative humidity for 36 hours.

| Sample | Layer melting point | Swelling 22° C H$_2$O in % | Wet scratch resistance in p/22° C | Wet scratch resistance at 38° C/developer in Pond |
|---|---|---|---|---|
| 1 without additive | 10'100° C | 330 | 400 | 250 |
| 2 | 10'100° C | 310 | 700 | 600 |
| 3 | 10'100° C | 290 | 1000 | 850 |
| 4 | 10'100° C | 320 | 700 | 450 |

The table shows that the velocity of hardening of the compounds according to the invention can be increased by the addition of water-soluble organic, low molecular weight solvents having boiling points above 100° C. The solvents act as water retaining agents so that when the layers are rapidly dried within 3 to 4 minutes, they contain more water after drying.

I claim:

1. A process of hardening a layer containing protein in a photographic material having at least one layer containing a light sensitive silver halide comprising incorporating a hardening amount of a hardener in the layer to be hardened
wherein the improvement comprises the hardener is partially hydrolyzed bis(dichlorotriazin-2-yl)-alkylamines or -arylamines.

2. A process of hardening a layer containing protein in a photographic material having at least one layer containing a light sensitive silver halide comprising incorporating a hardening amount of a hardener in the layer to be hardened
wherein the improvement comprises the hardener is a hardener of the general formula

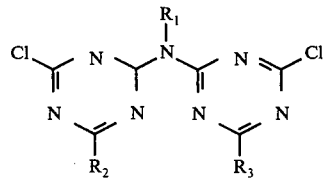

in which

R$_1$ represents hydrogen or an alkyl group with 1 to 3 carbon atoms unsubstituted or substituted with hydroxyl or halogen, an alkoxyalkyl group with 2 to 5 carbon atoms, a cycloalkyl group an aryl group unsubstituted or substituted, or the group

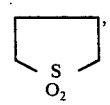

R$_2$ represents chlorine or R$_3$,
R$_3$ represents hydroxyl or —O$^-$ Me$^+$ represents an alkali metal or ammonium ion.

3. The process according to claim 2, characterised in that the hardener is left to act on the layer which is to be hardened in the presence of an organic water-miscible solvent having a boiling point of above 100° C.

4. The process according to claim 2 wherein the hardener is incorporated for hardening layers which contain, as binder, a protein selected from the group consisting of gelatine and carboxyl containing homopolymers and copolymers.

5. The process according to claim 2 wherein the hardener is applied from aqueous solution.

6. The process according to claim 2 wherein the hardener is applied from aqueous, sodium sulphate-containing solution.

7. The process according to claim 2 wherein the hardener is incorporated in quantities of from 0.2 to 8% by weight, based on the weight of the protein-containing binder in the casting solution of the layer which is required to be hardened.

8. The process according to claim 2 wherein the hardener is applied as a 0.1 to 10% solution before the photographic material is processed.

9. The process according to claim 2 wherein the layer which is required to be hardened is covered with a 0.1 to 10% solution of a hardener and then dried.

10. The process according to claim 2 wherein the hardener is incorporated in photographic multilayered materials.

* * * * *